United States Patent [19]

Zinnanti, Jr.

[11] Patent Number: 5,069,224

[45] Date of Patent: Dec. 3, 1991

[54] ENDOMETRIAL ASPIRATOR

[76] Inventor: Anthony Zinnanti, Jr., 13 Concho La., Bell Canyon, Calif. 91307

[21] Appl. No.: 535,125

[22] Filed: Jun. 8, 1990

Related U.S. Application Data

[63] Continuation of Ser. No. 314,948, Feb. 24, 1989, abandoned, which is a continuation of Ser. No. 181,367, Apr. 14, 1988, abandoned.

[51] Int. Cl.$^5$ ............................................. A61B 10/00
[52] U.S. Cl. .................................... 128/752; 128/758; 604/38
[58] Field of Search ......................... 128/749, 752, 758; 604/35, 36, 38, 54, 55, 121, 181, 187, 280–283, 264, 270

[56] References Cited

U.S. PATENT DOCUMENTS

| | | | |
|---|---|---|---|
| 3,561,429 | 2/1971 | Jewett | 128/752 |
| 4,534,362 | 8/1985 | Schumacher et al. | 128/749 |
| 4,662,869 | 5/1987 | Wright | 128/752 |
| 4,817,631 | 4/1989 | Schnepp-Pesch et al. | 128/749 |
| 4,819,635 | 4/1989 | Shapiro | 128/752 |
| 4,846,192 | 7/1989 | Stuart | 128/752 |

FOREIGN PATENT DOCUMENTS

| | | | |
|---|---|---|---|
| 1299588 | 3/1987 | U.S.S.R. | 128/749 |
| 1116465 | 6/1968 | United Kingdom | 128/752 |
| 2126100 | 3/1984 | United Kingdom | 128/749 |

*Primary Examiner*—Max Hindenburg
*Attorney, Agent, or Firm*—Allen A. Dicke, Jr.

[57] ABSTRACT

The endometrial aspirator has a tubular sheath or body which serves to receive a histological biopsy sample. The tube is closed at the distal tip and has a sample curette opening directly behind the tip. A rod extends to the opening, and at the proximal user end, extends out of the tubular body. The rod fits closely within the tube or preferably has an enlarged piston at the sample curette opening end. The distal tip is smooth, rounded and closed for ease of insertion. The body and rod are made of flexible material which is sufficiently stiff to prevent kinking during insertion.

18 Claims, 1 Drawing Sheet

ENDOMETRIAL ASPIRATOR

CROSS REFERENCE

This application is a continuation of my prior application Ser. No. 314,948, filed Feb. 24, 1989, abandoned, which, in turn, is a continuation of my prior application Ser. No. 181,367, filed Apr. 14, 1988, abandoned, for ENDOMETRIAL ASPIRATOR.

FIELD OF THE INVENTION

This invention is directed to an endometrial aspirator for taking uterine biopsies. The aspirator is sufficiently flexible for comfortable insertion and sufficiently stiff to prevent kinking.

For diagnostic purposes and for preventive medicine purposes, it is sometimes necessary to take endometrial (uterine) biopsies. Various samplers have been created for this purpose. The prior samplers have been cumbersome, which makes them difficult and painful to insert. Some have not delivered an adequate sample size, and others have not taken the sample from near the distal tip of the sampler, which is usually the desired histological biopsy sample location, thus keeping the sample uncontaminated by surrounding tissue such as endocervical cells.

SUMMARY

In order to aid in the understanding of this invention, it can be stated in essentially summary form that it is directed to an endometrial aspirator which has a tubular body containing a piston rod therein. The body is closed with a rounded tip, and directly behind the tip on the side of the body is the sample opening. The rod carries a piston therein which lies adjacent the sample opening, and when a sample is desired, the piston rod and piston are drawn back away from the tip to draw in a sample. The combined tube body and rod are sufficiently flexible to permit comfortable insertion without kinking.

It is thus an object and advantage of this invention to provide an endometrial aspirator which is easily and comfortably inserted and takes a sample from the desired location.

It is another object and advantage of this invention to provide an aspirator which is made of flexible synthetic polymer composition material with the material having such properties and being sized to be flexible without kinking.

It is another object and advantage of this invention to provide an endometrial aspirator made of synthetic polymer composition material so that it can be inexpensively made for economic, single use and disposal.

Other objects and advantages of this invention will become apparent from a study of the following portion of the specification, the claims and the attached drawings.

DESCRIPTION OF THE PREFERRED EMBODIMENT

Figure 1:
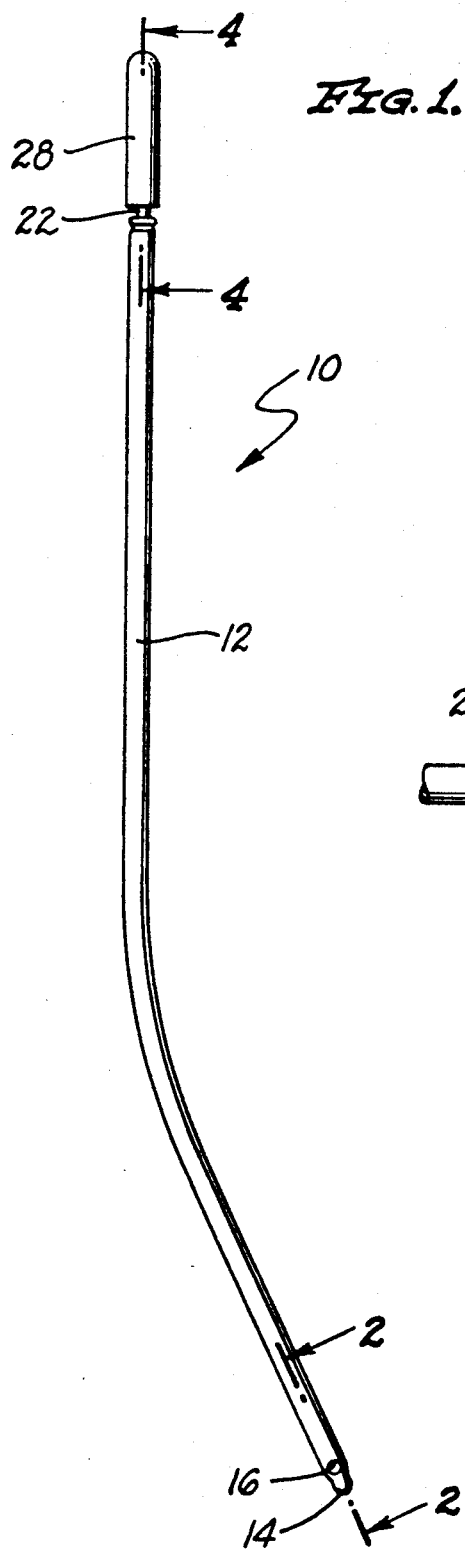
FIG. 1 is a side-elevational view of the endometrial aspirator of this invention.
Figure 2:
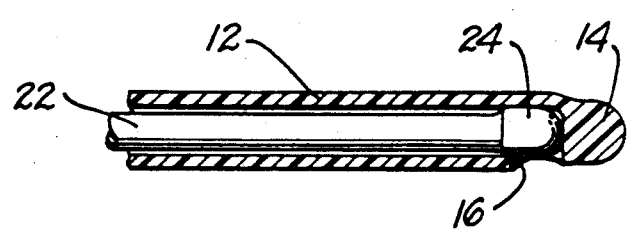
FIG. 2 is an enlarged central section through the tip distal portion of the aspirator, as seen generally along the line 2—2 of FIG. 1, with the piston in the forward position.
Figure 3:
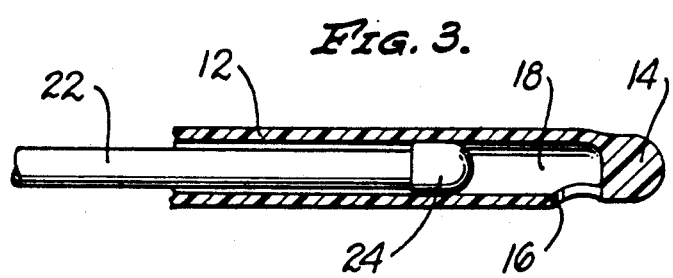
FIG. 3 is a similar view, showing partial withdrawal of the piston as in taking a sample.

Endometrial aspirator 10 is shown in an overall side-elevational view, partly bent, in FIG. 1. FIGURES 2 and 3 show the enlarged distal tip of the aspirator. The aspirator has a tubular sheath or body 12 which is a right circular cylindrical tube of substantially uniform wall thickness throughout its length. The body is made of thermoplastic synthetic polymer composition material, and by thermoplastic action, the distal tip 14 of tube 12 is closed to form an obturator for the tubular body. Tip 14 is smooth, tapered and rounded. About 0.8 millimeters behind the distal tip is curette or sample opening 16. The sample opening is about 2.4 millimeters in diameter, has sharp edges, and is open to the interior space 18 posterior to the obturator tip 14. The tubular body 12 terminates at proximal end 20, opposite the distal tip end.

Figure 4:
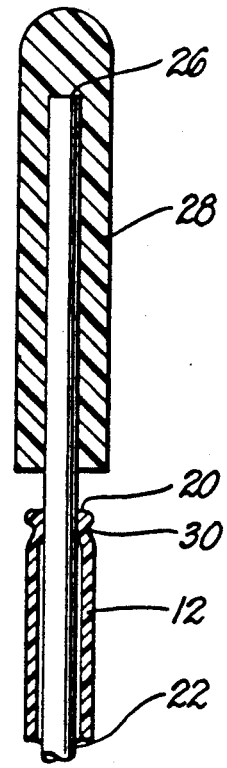
FIG. 4 is an enlarged section taken generally along the line 4—4 of FIG. 1, showing the user's proximal end of the aspirator.

Rod 22 extends through the tubular body 12 where piston 24 is formed on the rod and lies directly behind the obturator tip 14 when the rod is in its forward position, shown in FIG. 2. Piston 24 fits firmly within tubular body 12 so that withdrawal of the rod 22 causes the piston to draw a biopsy sample into the sample opening 16. Rod 22 extends out of the proximal end 20 to terminate in rod end 26, see FIG. 4. Handle 28 is secured to the rod where it extends out of the proximal end 20 of the tubular body, in order to aid in grasp and withdrawal of the rod and piston for sample taking.

All materials are preferably clear thermoplastic synthetic polymer composition material. The body is made of polypropylene and the piston rod, of soft acetal resin. The dimensions are such and flexibility of the polymer material is such that painless insertion can be made without dilation. As an example of flexibility, when the aspirator is about 25 centimeters long and is bent into a U with about 10 centimeters across the arms of the U, the force tending to return the aspirator to the straight position is about 70 grams. As an example of preferred dimensions, the tubular body 12 has an outside diameter of 3.1 millimeter and a wall thickness of about 0.25 millimeters. This leaves the interior diameter 18 at 2.6 millimeters in diameter. The rod 22 has a diameter of about 1.9 millimeters so that there is no friction between the rod and the tube walls as the piston is withdrawn. In order to make a close fit, the piston 24 has a diameter of about 2.8 millimeters. This provides an interference fit of about 0.2 millimeter on the diameter so that a good seal takes place. This seal is accomplished by the resiliency of the tubular walls of body 12. The body is preferably necked down at its proximal end 30 so that the proximal end of the body grasps rod 22. This neck has dual purposes. It prevents contaminants from entering the interior of the tubular body from the proximal end. This neck down also prevents withdrawal of the piston out of the proximal end, which might result in spillage of material and loss of the sample. The material from the aspirator is made is sterilizable so that the aspirator can be assembled, packaged and sterilized for sterile supply to the site of use. The aspirator is sufficiently inexpensive that it can be thrown away after use.

In use, the aspirator is removed from its sterile packaging and is inserted. The small volume of the sample opening 16, without any of the interior space of the tube open, prevents contamination of the endometrial sample to be taken with cervical cellular debris which might enter the aspirator if any significant volume was available. When the sample opening 16 is in place to take the desired endometrial sample, the handle 28 is grasped while the proximal end of the tubular body is held. The handle 28 is withdrawn to draw back piston 24 to supply maximum suction at the sample point. With the sample opening 16 on the side of the body, it will not be covered by tissue so that a proper sample can be taken. The piston is withdrawn by drawing on handle 28 a sufficient distance to take the desired sample volume. Thereupon, the entire endometrial aspirator is withdrawn from its sampling position and the aspirator is delivered to have its contents analyzed. In this way, the flexible aspirator with a rounded tip permits easy and painless insertion. The zero volume in the sample space during insertion prevents contamination by other cellular debris until the sample opening is in place and the piston is withdrawn.

This invention has been described in its presently contemplated best modes, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. An endometrial aspirator comprising:
   a flexible tubular body having closed walls defining an interior passage of uniform diameter throughout a substantial portion of its length, said flexible tubular body having a proximal end and a tip end, a closure on said tip end to close the tubular body at said tip end;
   walls defining a single sample opening aperture in the side of said body at said closure at said tip end, said single sample opening aperture being towards said proximal end of said body from said closure;
   a flexible rod in said interior passage in said tubular body, said flexible rod being smaller in diameter than the diameter of said interior passage to freely slide therein, said flexible rod having a flexible piston at its tip end, said piston engaging within and sealing against said passage walls of said tubular body, said piston being without a cutting edge, said piston lying directly against said closure at said closed tip end of said tubular body when in the forward position to substantially close said single sample opening aperture, said rod extending out of said proximal end of said tubular body so that said rod can be grasped to draw said piston through said tubular body to draw a vacuum in said body by withdrawal of said piston to draw a sample into said single sample opening aperture in the side of said tubular body so that the sample is drawn into said tubular body between said piston and said closure to retain the sample without cutting.

2. The endometrial aspirator of claim 1 wherein both said tubular body and said rod are made of flexible synthetic polymer composition material.

3. The endometrial aspirator of claim 2 wherein said synthetic polymer composition material of said body is thermoplastic and said closure forming said tip end closing said tubular body is thermoplastically formed of tubular body material to close the tip of said tubular body.

4. The endometrial aspirator of claim 3 wherein said synthetic polymer composition material of which said rod is made is thermoplastic and said piston on said rod is thermoplastically formed of the same material of which said rod is made.

5. The endometrial aspirator of claim 4 wherein said proximal end of said tubular body fits tightly around said rod to inhibit contamination from entering said tubular body and to inhibit withdrawal of said piston out of said tubular body.

6. The endometrial aspirator of claim 2 wherein said synthetic polymer composition material of which said rod is made is thermoplastic and said piston on said rod is thermoplastically formed of the same material of which said rod is made.

7. The endometrial aspirator of claim 1 wherein said proximal end of said tubular body fits tightly around said rod to inhibit contamination from entering said tubular body and to inhibit withdrawal of said piston out of said tubular body.

8. The endometrial aspirator of claim 7 wherein a handle is secured to said rod adjacent said proximal end of said tubular body to aid in grasp of said rod for withdrawing said piston from said closure forming said closed tip end to draw a sample into said tubular body.

9. An aspirator comprising:
   an elongated polymer composition material flexible tubular body defined by an outside wall and an inside wall forming a right circular cylindrical closed bore therein and having substantially uniform wall thickness, said body having a proximal end and a distal obturator end, said tubular body having a closure to close the bore at said obturator end and to form a rounded obturator tip, a single sample opening in the side wall of said tubular body at said closed distal obturator end of said body;
   a flexible rod of smaller diameter than said bore in said tubular body positioned within said bore in said tubular body to be freely slidable therein, said flexible rod having a proximal end and a distal end, said proximal end of said flexible rod extending out of the proximal end of said tubular body, said rod having a piston thereon at its distal end in sealing engagement with said tubular body, said piston lying against said inside wall of said bore against said distal obturator end closure and covering said single sample opening when said piston is in its forward position so that withdrawal of said rod pulls said piston through said tubular body back from said closure to uncover said single sample opening and to draw suction in the bore at said single sample opening to draw a sample into said tubular body through its single sample opening as said piston moves back from said closed distal obturator tip so that a sample is aspirated without cutting.

10. The aspirator of claim 9 wherein said tubular body is made of thermoplastic synthetic polymer composition material and said closure is unitarily formed thereon to close the tubular interior of said body at the distal end.

11. The aspirator of claim 10 wherein said rod is formed of thermoplastic synthetic polymer composition material and said piston is unitarily formed thereon, said piston having a larger diameter than the interior diameter of said tubular body to seal therein.

12. The aspirator of claim 11 wherein there is a handle on said rod adjacent said proximal end of said tubular body so as to enhance manual grip of said rod.

13. The endometrial aspirator of claim 9 wherein said tubular body has an outside diameter of substantially 3.1 millimeters and has a wall thickness of substantially 0.25 millimeters.

14. The aspirator of claim 13 wherein said piston has a diameter of about 2.8 millimeters and said rod is smaller than the interior bore of said tubular body.

15. The aspirator of claim 14 wherein said rod and said tubular body are sufficiently flexible so that when a 25 centimeter length there is bent into a U-shape having about 10 centimeters between the arms thereof, the resilient straightening force is about 70 grams.

16. The aspirator of claim 9 wherein said rod and said tubular body are sufficiently flexible so that when a 25 centimeter length thereof is bent into a U-shape having about 10 centimeters between the arms thereof, the resilient straightening force is about 70 grams.

17. An aspirator comprising:

an elongated polymer composition material flexible tubular body defined by an outside wall and an inside wall so as to form an enclosed bore having a substantially uniform circular cross section therein, said body having a proximal end and a distal end, said tubular body having a closure on the distal end thereof to close the bore at the distal end thereof, a single sample opening through the side wall of said tubular body at and proximal from said closure of said bore;

a flexible piston rod positioned within said tubular body and extending out of the proximal end of said tubular body, said rod being of smaller size than said bore to slide freely therein and having a piston thereon in sealing engagement with said inside wall of said tubular body, said piston lying at said closure and covering said single sample opening so that when said rod is withdrawn from said body, said rod pulls said piston through said tubular body away from said closure and away from said single sample opening towards said proximal end to create suction at said single sample opening to draw a sample into said tubular body through its single sample opening so that a sample is aspirated without cutting.

18. The aspirator of claim 17 wherein said piston, when in its position adjacent said distal end lies across the interior of said single sample opening so as to close said single sample opening to prevent material from passing into said bore when said piston is closing said single sample opening.

* * * * *